(12) United States Patent
Li et al.

(10) Patent No.: US 10,086,410 B2
(45) Date of Patent: Oct. 2, 2018

(54) APPARATUS, METHOD AND SYSTEM FOR WASHING OBJECTS WITH IRREGULAR SHAPES

(71) Applicants: Yongwang Li, Beijing (CN); Li Ma, Beijing (CN); Feng Ma, Cary, NC (US)

(72) Inventors: Yongwang Li, Beijing (CN); Li Ma, Beijing (CN); Feng Ma, Cary, NC (US)

(73) Assignee: Syncoda LLC, Cary, NC (US)

( * ) Notice: Subject to any disclaimer, the term of this patent is extended or adjusted under 35 U.S.C. 154(b) by 645 days.

(21) Appl. No.: 14/479,331

(22) Filed: Sep. 7, 2014

(65) Prior Publication Data
US 2015/0068553 A1     Mar. 12, 2015

(30) Foreign Application Priority Data

Sep. 11, 2013   (CN) .......................... 2013 1 0411391

(51) Int. Cl.
| | |
|---|---|
| *B01B 1/00* | (2006.01) |
| *B08B 1/00* | (2006.01) |
| *A47L 23/02* | (2006.01) |
| *B08B 3/04* | (2006.01) |
| *B08B 3/10* | (2006.01) |
| *A61B 90/70* | (2016.01) |

(52) U.S. Cl.
CPC ................ *B08B 1/00* (2013.01); *A47L 23/02* (2013.01); *B08B 3/044* (2013.01); *B08B 3/10* (2013.01); *A46B 2200/3073* (2013.01); *A61B 90/70* (2016.02)

(58) Field of Classification Search
None
See application file for complete search history.

(56) References Cited

U.S. PATENT DOCUMENTS

2002/0082188 A1\* 6/2002 Baker ..................... A47L 23/00
                                                                510/475
2003/0008799 A1\* 1/2003 Barnabas ............. C11D 3/2041
                                                                510/351

FOREIGN PATENT DOCUMENTS

CN            2910104 Y   \*  6/2007
CN          201106116 Y   \*  8/2008

\* cited by examiner

*Primary Examiner* — Katelyn B Whatley
(74) *Attorney, Agent, or Firm* — Syncoda LLC; Feng Ma; Junjie Feng

(57) ABSTRACT

An apparatus, system, and method allow for cleaning and brushing irregular-shaped objects automatically. The apparatus includes: an outer portion or a container that can substantially enclose one or more irregular shaped objects, and a plurality of brushes movably coupled to an inner wall of the outer portion or the container. The apparatus can be used to wash irregular-shaped objects such as shoes, utensils, medical devices, etc. An irregular-shaped object can be placed in the apparatus, and the apparatus can be placed in a washing machine for automatic washing. Driven by a flow of water, air, or gas, the brushes can scrub the object. The apparatus can protect the object from potential damages, and/or keep washed-off sand, dirt, or other residues inside the apparatus.

20 Claims, 5 Drawing Sheets

APPARATUS, METHOD AND SYSTEM FOR WASHING OBJECTS WITH IRREGULAR SHAPES

CROSS-REFERENCE TO RELATED APPLICATIONS

The present application is a continuation of, and claims priority to, Chinese Patent Application No. CN 201310411391.1 filed on Sep. 11, 2013, the disclosure of which is hereby incorporated by reference in its entirety.

BACKGROUND

For objects having regular shapes, or objects having irregular shapes but with flexible texture (for example, clothing), automatic washing and cleaning can be achieved using appliances such as washing machines or washing cabinets. Objects with irregular shapes and relatively rigid texture, such as containers, medical utensils with hollow interiors, and shoes, etc., usually need to be washed manually using brushes.

SUMMARY

An apparatus, system, and method allow for cleaning and brushing irregular-shaped objects automatically. The apparatus includes: an outer portion or a container that can substantially enclose one or more irregular shaped objects, and a plurality of brushes movably coupled to an inner wall of the outer portion or the container. The apparatus can be used to wash irregular-shaped objects such as shoes, utensils, medical devices, etc. An irregular-shaped object can be placed in the apparatus, and the apparatus can be placed in a washing machine for automatic washing. Driven by a flow of water, air, or gas, the brushes can scrub the object. The apparatus can protect the object from potential damages, and/or keep washed-off sand, dirt, or other residues inside the apparatus. The washing machine or washing cabinet can be sold together with the apparatus, or it can be an upgraded from a conventional household appliance, with the disclosed apparatus as a component or accessory.

Various features are described in detail below with various embodiments and drawings.

In an aspect, a washing apparatus is provided and configured to wash an object with an irregular shape, the apparatus including: an outer portion configured to substantially enclose the object; and a plurality of brushes movably coupled to an inner wall of the outer portion.

In some embodiments, the outer portion has a plurality of holes with a size of about 1 μm to about 10 cm.

In some embodiments, the size of the holes is about 0.5 mm to about 2 mm.

In some embodiments, the size of the holes is about 1 mm.

In some embodiments, the outer portion is flexible, wherein the outer portion and the plurality of brushes are configured to conformally enclose the object, and wherein the plurality of brushes are movably coupled with the inner wall of the outer portion.

In some embodiments, the outer portion is rigid, wherein the outer portion comprises a plurality of outer frames, and wherein the plurality of brushes are rotatably coupled with the plurality of outer frames.

In some embodiments, the plurality of brushes comprise one or more protrusions.

In some embodiments, the apparatus further comprises a smaller container configured to carry and dispense a detergent.

In another aspect, a washing system is provided including: a washing machine or a washing cabinet; and a washing apparatus configured to wash an object with an irregular shape, the apparatus including: an outer portion configured to substantially enclose the object; and a plurality of brushes movably coupled to an inner wall of the outer portion In some embodiments, the washing apparatus together with the object enclosed therein are configured to be placed in the washing machine or the washing cabinet for automatic washing.

In some embodiments, the washing apparatus is coupled to a bracket, and wherein the bracket is configured to rotatably or extendably place the washing apparatus into a washing space of the washing machine or washing cabinet.

In some embodiments, the washing apparatus is configured to wash shoes, and wherein the washing machine or the washing cabinet is a household washing machine.

In some embodiments, the washing system further includes a plurality of brushes forming an array configured to have a plurality of objects fitted thereto and have rotational motions as a result from impact by water flows.

In some embodiments, the washing system further includes a smaller container configured to carry and dispense a detergent inside the apparatus.

In another aspect, a method is provided including: disposing an irregular-shaped object inside an outer portion of a washing apparatus such that the outer portion substantially conformally encloses the object; and driving, with a flow of water, air, or gas, a plurality of brushes movably coupled to an inner wall of the outer portion to scrub the object.

In some embodiments, the method further includes placing the washing apparatus with the irregular-shaped object enclosed therein into a washing machine for automatic washing, wherein the flow of water or air is provided by the washing machine.

In some embodiments, the placing comprises rotatably or extendably placing with a bracket.

In some embodiments, the method further includes dispensing a detergent inside the apparatus from a smaller container inside the outer portion.

In some embodiments, the washing apparatus is flexible and together with the brushes are configured to conform substantially to a shape of the irregular-shaped object.

In some embodiments, the washing apparatus has a plurality meshed holes thereon to allow water, air, or gas to communicatively flow between inside and outside of the washing apparatus.

DETAILED DESCRIPTION

Features of a washing apparatus, system, and method according to some embodiments are described below with reference to the drawings.

Figure 1:
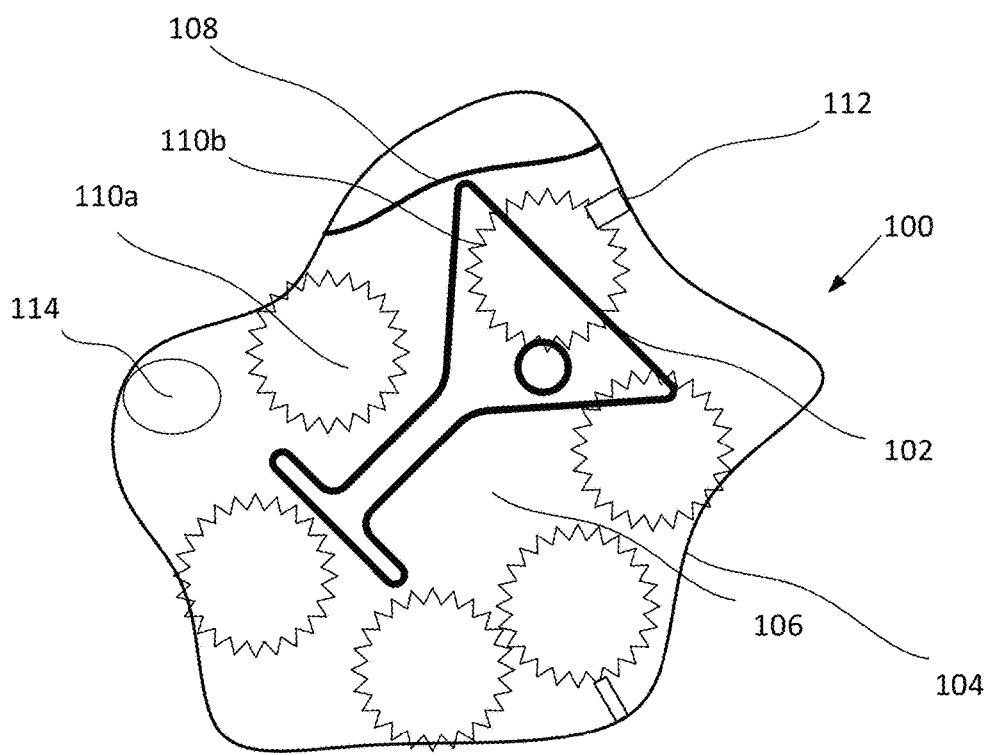
FIG. 1 illustrates an embodiment of a washing apparatus for washing objects with irregular shapes.

FIG. 1 illustrates a washing apparatus configured to washing object(s) with irregular shape(s) according to some embodiments.

As shown in FIG. 1, a washing apparatus 100 is configured to wash an irregular-shaped object 102, such as a glass utensil. Irregular shaped objects 102 can also be shoes, medical instruments/devices or other irregular-shaped objects. Such medical instruments can be gynecological speculums, straws, curettes, or a variety of surgical instruments such as forceps, scissors, curved plates, and hooks, etc.

The washing apparatus 100 for brushing/washing irregular shaped objects can include an outer portion or a container, an outer frame, or an outer sidewall 104, which can be flexible and made of fabrics, acrylics, polyesters, plastics, or rubber, etc.

The outer portion 104 can include a plurality of holes 106, such as mesh holes, which allow water or a cleaning liquid to flow through the outer portion 104 communicatively between inside and outside. In some embodiments, the holes can be squared, circular or of any other shapes, and their typical sizes can be between 1 μm and 10 cm, for example. In some embodiments, the typical sizes of openings are between 0.5 and 2 mm, for example, approximately 1 mm, which allow the water or the cleaning liquid to flow through the outer portion 104 communicatively inside and out, while still keeping the rinsed-off residues (for example, food residues, or sand and dirt off shoes) inside the outer portion 104 of the apparatus to avoid sewer drain clog. In other embodiments, the typical size of the holes is about 0.1 mm.

The outer portion 104 can also include a larger opening 108 to load the irregular-shaped object 102 therethrough. The opening 108 can be substantially closed using a zipper or a cord, to thereby secure the irregular-shaped object 102 in the apparatus during wash without dropping out of the apparatus. The size of the larger opening 108 can be comparable to the size of the irregular-shaped object 102, and can be for example, greater than 10 cm.

The inner sidewall of the outer portion 104 can have one or more brushes 110a, 110b . . . , coupled therein. The brushes 110 can be spherical, circular, rectangular, etc., and can be made of common materials, for example including a plurality of plastic bristles.

In some embodiments, the brushes 110a can be directly fastened (for example, sewed) to the inner sidewall of the outer portion 104. Because the outer portion 104 can be flexible, the brushes 110a can be movable under the effect of water stream or pressing from other objects, and thereby realizing scrubbing and brushing actions toward the irregular-shaped object 102.

In some embodiments, the coupling is flexible, and it can be realized, for example, by using a coupler 112. The coupler 112 can be a short string, a rubber band, a spring, or a cord, etc., and the material for the coupler can be fabrics, plastics, rubber, or metal, etc. By using a flexible coupler 112, for example, a rubber band or a spring, the radial degree of freedom of the brush 110b can be increased.

In some embodiments, the outer portion 104 can be tensible, which together with the plurality of brushes 110a, 110b, . . . can substantially conformally enclose the irregular-shaped object 102. The plurality of brushes can come into contact with and scrub and brush the inside and outside of the irregular shaped object 102. In some embodiments, tensibility of the outer portion 104 can be achieved through a few elastic core ropes/cords, such as elastic cords or rubber bands. In some other embodiments, main composition materials of the outer portion 104 can be all tensible. Such a tensible conformal enclosing configuration allows washing of objects with different sizes, facilitating contact of the brushes with recessed portions of the irregular-shaped object 102, and providing a pressure at the contact points, thereby helping with the scrubbing and brushing process.

In some embodiments, each irregular-shaped-object brushing and washing apparatus 100 can enclose one object 102 during the wash. In some other embodiments, each apparatus 100 can enclose a plurality of objects during the wash. For example, each irregular-shaped-object brushing and washing apparatus 100 can simultaneously enclose a pair of shoes to avoid shoe pair mismatch after the wash. In some embodiments, the irregular-shaped-object brushing and washing apparatus 100 can have just one inner chamber, and a plurality of objects can be contained and washed in the same chamber. In some other embodiments, the irregular-shaped-object brushing and washing apparatus 100 can have multiple chambers, for example two chambers, each enclosing a shoe. The multiple chambers and the outer portion 104 can be made of similar or different materials/textures.

In some embodiments, a mesh structure can be formed from direct connections of a plurality of brushes 110a, 110b . . . without the outer portion 104. In some other embodiments, the mesh structure formed from direct connection of a plurality of brushes 110a, 110b . . . can be placed in the outer portion 104 to form flexible couplings, without being fastened/sewed to the inner sidewall of the outer portion 104.

In using some embodiments of the irregular-shaped-object brushing and washing apparatus 100 of FIG. 1, the apparatus can enclose an irregular-shaped object 102, and be placed in a washing machine together with other apparatuses or clothing for cleaning and washing using a normal wash mode. Because the irregular-shaped object 102 is enclosed by the apparatus 100 and/or a plurality of brushes 110a, 110b . . . , it can be protected from damages caused by collision with other objects and the inner wall of the washing machine.

In some embodiments, the apparatus 100 can include one or more smaller containers 114, which can be placed in the apparatus 100 and/or can be coupled to the inner sidewall of the apparatus 100. The small container 114 can be used to carry a liquid, solid, or powdered detergent. The small container 114 can be configured to slowly release/dispense the detergent in order to enhance the washing efficiency of the irregular-shaped object 102.

The brushing and washing apparatuses 100 can be provided to users individually, and the users can use them in conjunction with their own washing machines/washing cabinets. In another aspect, a washing system is disclosed herein, which comprises the irregular shaped object brushing and washing apparatus(es), and a washing machine or a washing cabinet.

In some embodiments, the irregular-shaped-object brushing and washing apparatus(es), along with the irregular-shaped objects enclosed therein, can be placed in the washing machine or washing cabinet for automatic washing.

In some embodiments, the brushing and washing apparatus can be coupled to a support structure, and the support structure can rotatably or extendably place the brushing and washing apparatus into the washing space inside the washing machine or washing cabinet.

In some embodiments, the irregular-shaped-object brushing and washing apparatus can be a shoe brushing apparatus, and the washing machine or washing cabinet can be a household washing machine. Users can place the shoe(s) in the apparatus(es), and place the apparatus(es) and the enclosed shoe(s) in the washing machine(s) together with other such apparatuses containing irregular shaped objects or clothes. The washing process can be the same as or similar to a clothes washing process.

Figure 2:
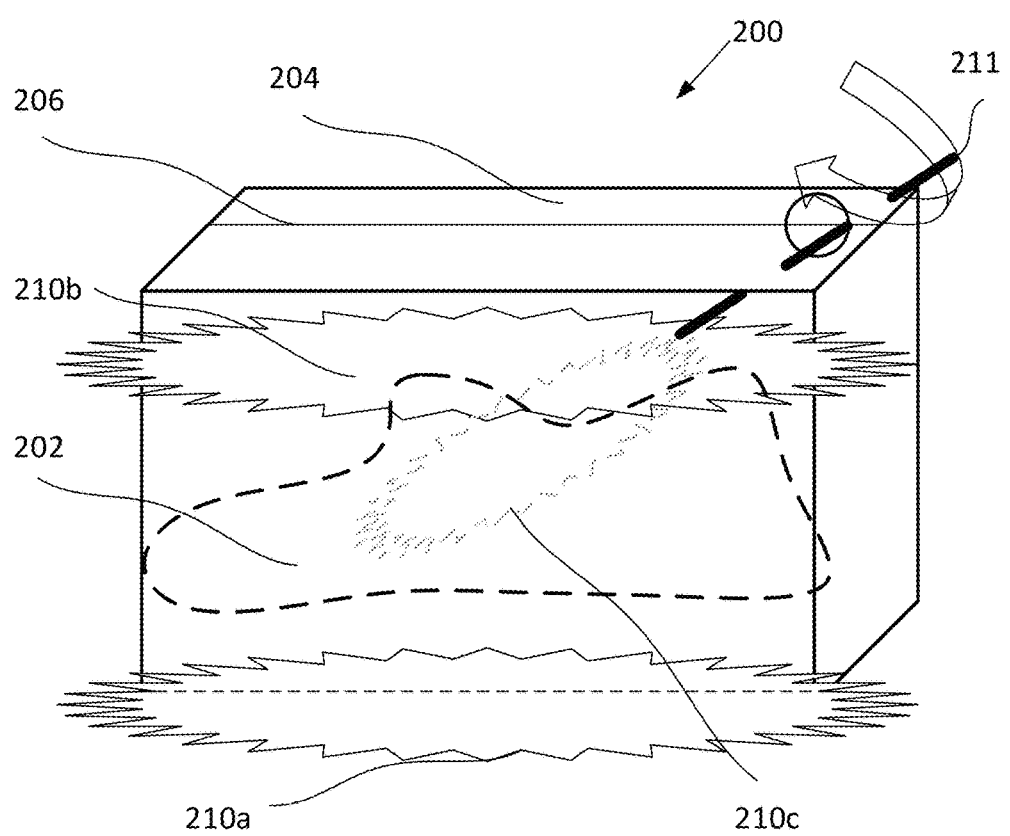
FIG. 2 illustrates another embodiment of a washing apparatus.

FIG. 2 illustrates another embodiment of an irregular-shaped-object brushing and washing apparatus, system, and method. As shown in FIG. 2, an irregular-shaped-object brushing and washing apparatus 200 can be used to wash an irregular-shaped object 202 (for example, a shoe). The irregular-shaped-object brushing and washing apparatus 200 can have an outer portion 204, which can include a plurality of outer frames 206. The outer frames 206 can be substantially rigid, or flexible.

The outer portion 204 can be coupled with a plurality of brushes 210a, 210b . . . . The brushes can be elongated, circular, spherical, or of other shapes. The brushes 210a, 210b . . . can each rotate around its rotation axis, such as using an outer frame as an axis, under the effect whirling water stream or pressing from other objects/washing apparatuses during the wash. Bristles of the brushes 210a, 210b . . . can thus brush the object 202 during the rotations.

One or more brush 210c can be inserted into the interior of the irregular-shaped object 202 (for example, the interior of a shoe) with an angle. The brush 210c can have a rotation axis 211, which can be movably coupled to the outer frame 206. The coupling can be realized by using a coupler 212 (for example, a ring). Being impinged upon by the water stream, the brush 210c can rotate around or together with the rotation axis 211 to scrub the interior of shoe 202, but also being prevented from departing the outer frame 206 as a result of the constraint from the coupler 212.

In some embodiments, the brushing and washing apparatus 200 of FIG. 2 can enclose an irregular-shaped object 202 and be placed in a washing machine together with other apparatuses or clothes for washing using a normal wash mode (for example, following the water stream rather freely). The brushing and washing apparatus 200 and/or a plurality of brushes 210a, 210b . . . enclose the irregular-shaped object 202 and protect it from potential damages caused by collisions with other objects or the inner sidewall of the washing machine. Although a shoe is used as an example for an irregular-shaped object in FIG. 2, the irregular-shaped object 202 can be a utensil, etc.

Figure 3:
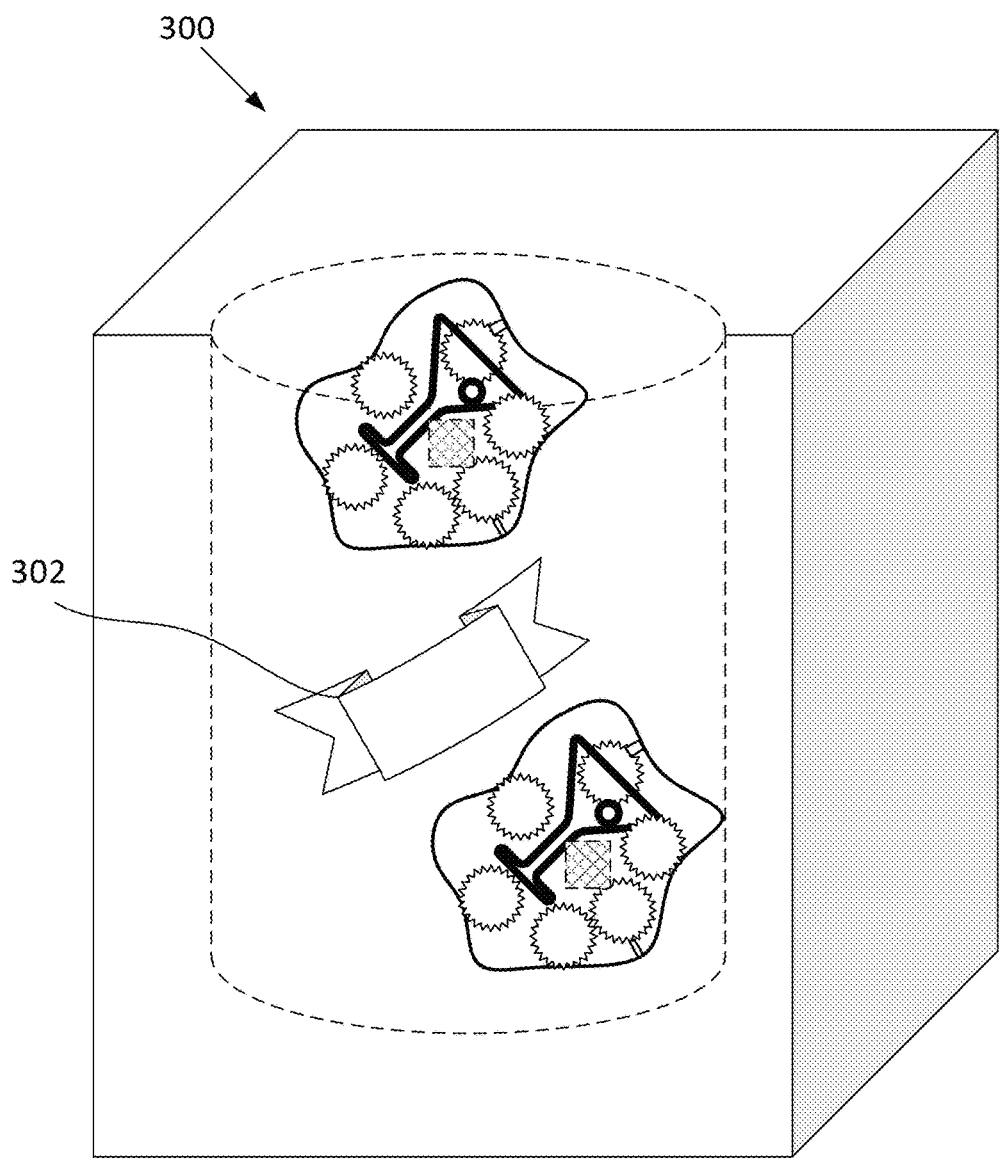
FIG. 3 illustrates a washing system according to some embodiments.

FIG. 3 illustrates some embodiments wherein a plurality of brushing and washing apparatuses enclosing irregular-shaped objects are placed in a washing machine or washing cabinet 300 for automatic washing. The example irregular-shaped objects in FIG. 3 are glass goblets, but such irregular-shaped objects can also be shoes, etc. Clothes 302 and other objects can be washed in a washing machine at the same time, and they can buffer or mitigate the collisions between the irregular shaped objects, which are enclosed by the apparatuses, and other objects. In some embodiments, the brushing and washing apparatuses can keep the rinsed-off residues (for example, sand and dirt, fabric fibers, etc.) inside the apparatuses.

In some other embodiments, the brushing and washing apparatus 100 of FIG. 1 or 200 of FIG. 2 can be hung on a rack fixed to the inner wall of the washing machine.

Figure 4:
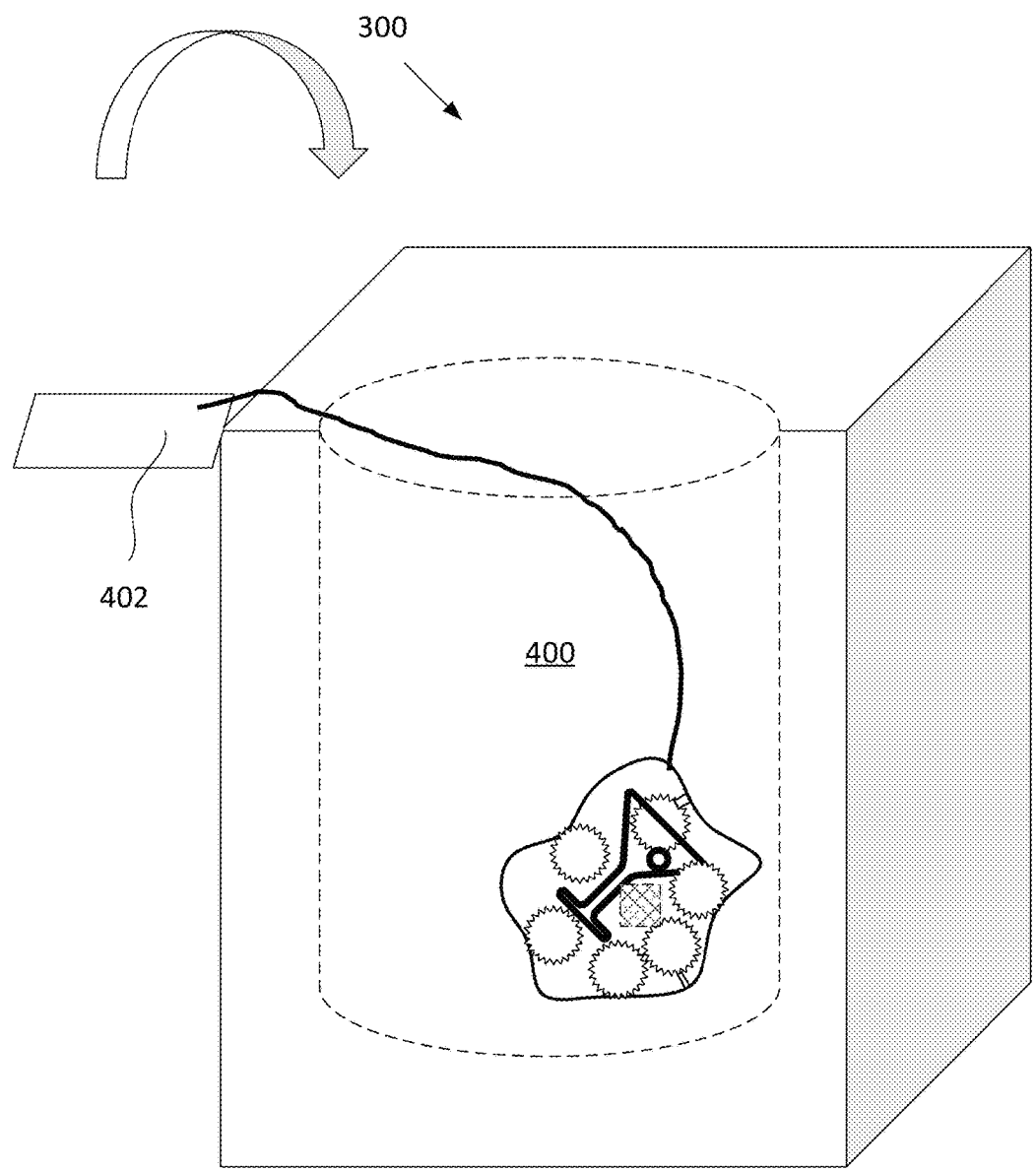
FIG. 4 illustrates a washing method according to some embodiments.

In some other embodiments, as shown in FIG. 4, the brushing and washing apparatus 100 of FIG. 1 and 200 of FIG. 2 can be an accessory of a washing machine/washing cabinet 300, and can extend out or flip outward into the washing space 400 of the washing machine via a bracket 402. Extension and retraction can be realized through flexible or rigid connections; can be telescopic, or hinge/bending types of connections.

Figure 5:
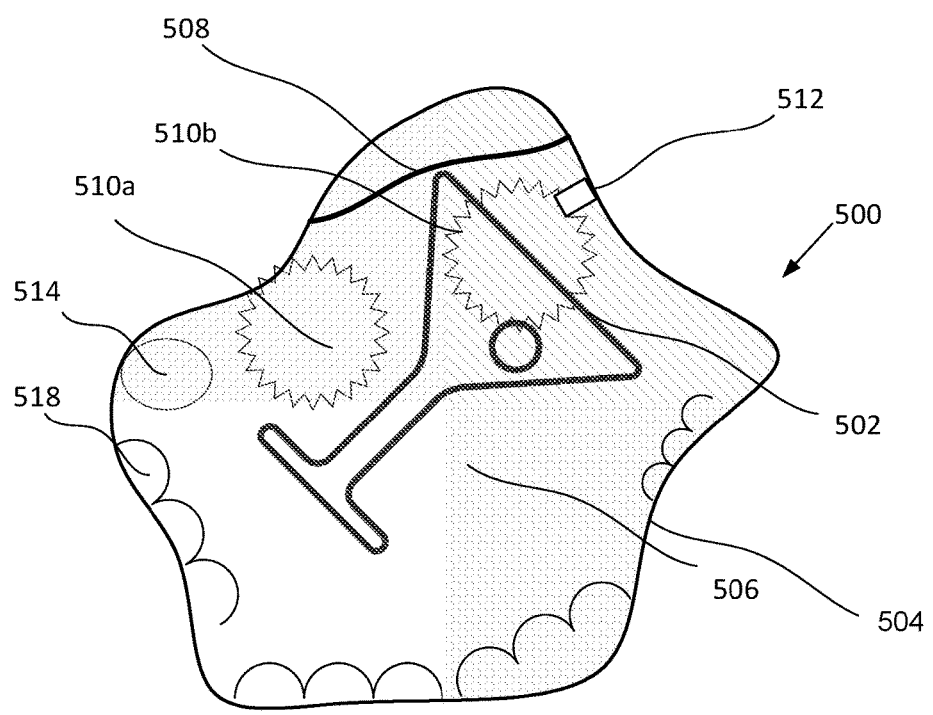
FIG. 5 illustrates a washing apparatus according to some other embodiments.

FIG. 5 illustrates another embodiment of the irregular-shaped-object brushing and washing apparatus, system, and method.

As shown in FIG. 5, an irregular-shaped-object brushing and washing apparatus 500 can be used to wash an irregular-shaped object 102, shown in the example as a utensil 502, but the irregular-shaped objects can be shoes, medical instruments, etc. The medical instruments can be gynecological devices such as speculums, straws, curettes, or a variety of surgical instruments such as forceps, scissors, curved plates, and hooks.

The irregular-shaped-object brushing and washing apparatus 500 can include an outer portion 504, which can be flexible as shown in FIG. 5. The outer portion 504 can be made of fabrics, acrylics, polyesters, plastics, or rubber, etc.

The outer portion 504 can comprise a plurality of holes or openings 506, such as meshed holes, which allow water or a cleaning liquid to flow through the outer portion 504 communicatively between the inside and outside. In some embodiments, the holes can be squared, circular, or of any other shapes, with typical dimensions between 1 µm and 10 cm. In some embodiments, the typical hole size is configured to be between 0.5 mm and 2 mm, for example about 1 mm, which allows water or cleaning liquid to flow through the outer portion 504 while still keeping the rinsed-off residues (for example, food residues, or sand and dirt off shoes) inside the outer portion 504, to avoid sewer drain clog. In some other embodiments, the typical hole size is about 0.1 mm.

The outer portion 504 can also comprises a larger opening 508 for loading an irregular-shaped object 502. The opening 508 can be substantially closed using a zipper, an elastic band, or a cord, keeping the irregular-shaped object 502 inside the apparatus during wash without getting out. The size of the large opening 508 can be comparable to the size of the irregular shaped object 502, for example, greater than 10 cm.

The inner wall of the outer portion 504 can have one or more brushes 510a, 510b coupled thereon. The shape of brushes 510a, 510b . . . can be spherical, circular, rectangular, etc. The brushes can be made of common materials such as plastics bristles.

In some embodiments, the brushes 510a can be directly fastened (for example, sewed) to the inner wall of the outer portion 504. Because the outer portion 504 can be flexible, the brushes 510a can be movable under the effect of whirling water stream or pressing from other objects, and thus realizing scrubbing and/or brushing of the irregular-shaped object 502.

In some embodiments, the couplings can be flexible, and can be realized by, for example, using a coupler 512. The coupler 512 can be a short string, a rubber band, a spring, a cord, etc. The material of coupler 512 can be fabrics, plastic, rubber, or metal, etc. By using a flexible coupler 512 (for example, a rubber band or a spring), brush 510b's radial degree of freedom can be increased.

In some embodiments, the outer portion 504 can be tensible, and it can conformally enclose an object with a plurality of brushes 510a, 510b . . . . Multiple brushes can thus scrub and wash the exterior and interior of object 502.

In using some embodiments of the irregular-shaped-object brushing and washing apparatus, the brushing and washing apparatus 500 in FIG. 5 can enclose an irregular-shaped object 502, and be placed in a washing machine alone or together with other apparatuses and clothes for cleaning using a normal wash mode. Because the irregular-shaped object 502 is enclosed by the apparatus 500 and/or the multiple brushes 510a, 510b . . . , the irregular-shaped object 502 can be protected from potential damages caused by its collision with other objects or the inner wall of the washing machine.

In some embodiments, the brushing and washing apparatus 500 can further comprise one or more small containers 514, which can be placed in the apparatus and/or coupled to the inner wall of brushing and washing apparatuses 500. The small containers 514 can be used to carry a liquid, solid, or powdered detergent. The small containers 514 can be configured to slowly release the detergent to enhance the washing efficiency of the irregular shaped object 502.

In some embodiments, the plurality of brushes 510a, 510b . . . , the coupler 512, and the small containers 514 can be optional. A plurality of protrusions 518 can be coupled, directly sewed, or directly formed on the inner wall of the outer portion 504. The protrusions 518 can be tensible, and made of rubber or plastic, and can be hemispherical, spherical, circular, or any other shapes. The diameters of the protrusions can be between 1 µm to 5 cm (for example, 0.5 cm); the heights can be between 1 mm to 5 mm (for example, 0.3 cm). The protrusions 518 can be fixed by direct insertion, sewing, or direct formation of bristles on the inner sidewall of the outer portion 504. Brushing and washing of the irregular-shaped object 502 using the plurality of protrusions 518 can be realized under the effect of water flow and pressing from other apparatuses, the inner sidewall of the washing machine, or other clothes, resembling the working mechanism of washboards. A plurality of protrusions 518 and brushes 510b can be used together, wherein brushes 510b may be more suitable for scrubbing the interior of an irregular-shaped object 502, for example, a shoe.

In some other embodiments, the washing machine/washing cabinet can have a plurality of brushes disposed therein forming an array, such that multiple irregular-shaped objects can be fit to the brushes, having a rotational motion as a result from impact by water flows, thereby being cleaned.

In some embodiments, the movement of the apparatus and/or the brushes are driven by a flow of water, air, or gas (such as inert gas in some special areas of applications) provided by automatic washing machines/cabinets. Without modifying existing washing machines/cabinets, the flow generated therein may be sufficient to drive the brushes to have complex movements to scrub the irregular-shaped objects thoroughly. The washing can be done on a smaller household scale, or an industrial scale for automatic washing of a large number of irregular-shaped objects concurrently.

The above drawings and specifications have illustrated various examples embodiments, and thus on this basis various modifications and improvements will become obvious to those of ordinary skill in the art. Therefore, the nature and the scope of protection of the present invention shall be broadly interpreted, as claimed in the attached claims, but shall not be limited to the above specifications.

The invention claimed is:

1. A washing apparatus configured to wash an object with an irregular shape, the apparatus comprising:
   an outer portion configured to substantially enclose the object; and
   a plurality of brushes movably coupled to an inner wall of the outer portion with one or more couplers comprising at least one of a string, a rubber band, a spring, or a cord, wherein:
   the washing apparatus is configured to be disposed inside a washing machine or washing cabinet; and
   the plurality of brushes are configured to scrub the object by motions between the plurality of brushes and the object resulting from a flow in the washing machine or washing cabinet.

2. The washing apparatus of claim 1, wherein the outer portion has a plurality of holes with a size of about 1 µm to about 10 cm.

3. The washing apparatus of claim 2, wherein the size of the holes is about 0.5 mm to about 2 mm.

4. The washing apparatus of claim 3, wherein the size of the holes is about 1 mm.

5. The washing apparatus of claim 1, wherein the outer portion is flexible, wherein the outer portion and the plurality of brushes are configured to conform around the object, and wherein the couplers are flexible and are made of at least one of fabrics, plastics, rubber, or metal.

6. The washing apparatus of claim 1, wherein the outer portion is rigid, wherein the outer portion comprises a plurality of outer frames, and wherein the plurality of brushes are rotatably coupled with the plurality of outer frames.

7. The washing apparatus of claim 1, wherein the plurality of brushes comprise one or more protrusions.

8. The washing apparatus of claim 1, further comprising a container configured to carry and dispense a detergent.

9. A washing system comprising:
   a washing machine or a washing cabinet; and
   a washing apparatus configured to wash an object with an irregular shape, the apparatus including:
   an outer portion configured to substantially enclose the object; and
   a plurality of brushes movably coupled to an inner wall of the outer portion with one or more couplers comprising at least one of a string, a rubber band, a spring, or a cord, wherein:
   the washing apparatus is configured to be disposed inside the washing machine or washing cabinet; and
   the washing machine or washing cabinet is configured to have a flow therein to cause motions between the brushes and the object to thereby scrub the object with the brushes.

10. The washing system of claim 9, wherein the washing apparatus together with the object enclosed therein are configured to be placed in the washing machine or the washing cabinet for automatic washing, and wherein the couplers are flexible and are made of at least one of fabrics, plastics, rubber, or metal.

11. The washing system of claim 9, wherein the washing apparatus is coupled to a bracket, and wherein the bracket is configured to rotatably or extendably place the washing apparatus into a washing space of the washing machine or washing cabinet.

12. The washing system of claim 9, wherein the washing apparatus is configured to wash shoes, and wherein the washing machine or the washing cabinet is a household washing machine.

13. The washing system of claim 9, further comprising a plurality of brushes forming an array configured to wash a plurality of objects with rotational motions as a result from impact by water flows.

14. The washing system of claim 9, further comprises a container configured to carry and dispense a detergent inside the apparatus.

15. A method comprising:
   disposing an irregular-shaped object inside an outer portion of a washing apparatus such that the outer portion substantially conforms around the object; and driving, with a flow of water, air, or gas, a plurality of brushes movably coupled to an inner wall of the outer portion to scrub the object, wherein:

the washing apparatus comprises:

the outer portion configured to substantially enclose the object; and the plurality of brushes movably coupled to the inner wall of the outer portion with one or more couplers comprising at least one of a string, a rubber band, a spring, or a cord;

the washing apparatus is configured to be disposed inside a washing machine or washing cabinet; and the plurality of brushes are configured to scrub the object by motions between the plurality of brushes and the object resulting from a flow in the washing machine or washing cabinet.

16. The method of claim 15, further comprising placing the washing apparatus with the irregular-shaped object enclosed therein into the washing machine or washing cabinet for automatic washing, wherein the flow of water or air is provided by the washing machine or washing cabinet.

17. The method of claim 16, wherein said placing comprises rotatably or extendably placing with a bracket.

18. The method of claim 17, further comprising dispensing a detergent inside the apparatus from a container inside the outer portion.

19. The method of claim 15, wherein the washing apparatus is flexible and together with the brushes are configured to conform substantially to a shape of the irregular-shaped object, and wherein the couplers are flexible and are made of at least one of fabrics, plastics, rubber, or metal.

20. The method of claim 19, wherein the washing apparatus has a plurality meshed holes thereon to allow water, air, or gas to communicatively flow between inside and outside of the washing apparatus.

\* \* \* \* \*